United States Patent [19]

Gupte et al.

[11] Patent Number: 4,574,052
[45] Date of Patent: Mar. 4, 1986

[54] CRACKLING AEROSOL FOAM

[75] Inventors: Anil J. Gupte, Seymour; Joyce M. Kendall, Huntington, both of Conn.

[73] Assignee: Richardson-Vicks Inc., Wilton, Conn.

[21] Appl. No.: 615,574

[22] Filed: May 31, 1984

[51] Int. Cl.$^4$ .......................... C11D 17/00; C09K 3/30
[52] U.S. Cl. ................................. 252/90; 252/174.16; 252/174.21; 252/174.25; 252/305; 252/DIG. 5; 252/DIG. 13; 424/45; 424/47
[58] Field of Search ................ 252/90, 305, DIG. 13, 252/DIG. 5; 424/47, 45

[56] References Cited

U.S. PATENT DOCUMENTS

| | | | |
|---|---|---|---|
| 3,639,568 | 2/1972 | Schmitt | 252/305 X |
| 3,728,265 | 4/1973 | Cella et al. | 252/90 |
| 3,728,276 | 4/1973 | Lieberman et al. | 252/305 |
| 3,770,648 | 11/1973 | Mackles | 252/305 |
| 3,947,568 | 3/1976 | Bates et al. | 424/47 |
| 4,182,688 | 1/1980 | Murtaugh | 252/305 |

FOREIGN PATENT DOCUMENTS 0029563 3/1980 Japan ........................ 252/DIG. 13

*Primary Examiner*—Richard D. Lovering
*Attorney, Agent, or Firm*—George W. Rauchfuss, Jr.; Salvatore R. Conte

[57] ABSTRACT

Aerosol foams producing a pronounced and prolonged auditory effect upon discharge from an aerosol container are provided by a foamable aerosol composition containing zeolite, surfactant, vehicle and liquified gas propellant.

20 Claims, No Drawings

CRACKLING AEROSOL FOAM

FIELD OF THE INVENTION

This invention relates to aerosol type foam compositions characterized by pronounced auditory effects, such as pinging and popping sounds, when compositions are discharged from aerosol containers.

BACKGROUND OF THE INVENTION

It has long been recognized as desirable to provide various types of products in foam form such as for example, skin and oral cleansers, shampoos, household cleansers, deodorants, insecticide sprays, household waxes, hair sprays, cosmetics and the like. In said products gases may be allowed to be released from the compositions in which they have been previously dissolved or liquified gases are retained in the liquid phase with only slow boiling occurring at temperatures which are significantly higher than the boiling point of these liquids at the prevailing environmental pressure.

In many instances it is highly desirable that such products be capable of producing auditory or continued bubbling effects long after the discharge of the product from the aerosol container. Such an effect is particularly desirable in personal care and cosmetic type products wherein the continued popping, pinging or bubbling effect produces a tingling sensation which is imparted to the body surfaces and the auditory effect acts as an indicator of the presence and continued action of the product.

Heretofore bubbling or effervescent products have generally been limited to product types in which dissolved gases, suoh as carbon dioxide, are permitted to be released from solutions in which they have been previously dissolved, e.g. carbonated beverages, or where gases are created by chemical reaction during or immediately preceding the time of use of those products, such as for example, by the reaction of an acidic component with a carbonate or bicarbonate and the release of carbon dioxide thereby. In addition to the limit of the type of products that may be involved, the bubbling is generally of very short duration.

It would therefore be highly desirable to be able to produce a wide variety of foam products characterized by a pronounced auditory effect, such as pinging and popping sounds, maintained over a substantial period of time.

SUMMARY OF THE INVENTION

It has been found that a composition comprising, as the foam and auditory sensation producing components, by weight, from about 16.0 to about 34.0% molecular sieve (zeolite), about 1.6 to about 3.4% surfactant, about 22.4 to about 47.6% vehicle and about 15.0 to about 60.0% liquified gas propellant, when dispensed from an aerosol container produces a crackling foamed composition characterized by a pronounced, prolonged auditory effect, such as pinging and popping sounds. When the pressure in a pressurized aerosol container of this invention is released by means of a valve on the aerosol container the contents of this pressurized container are discharged and any untrapped liquified gas propellant which is discharged from the container vaporizes substantially instantaneously and forms a foam of the contents as the contents of the aerosol container enter the lower pressure zone of the atmosphere. However, the zeolite material discharged from the aerosol container retains a substantial portion of the liquified gas propellant trapped in the pores thereof and this trapped propellant is slowly released from the zeolite pores over a period of time and bubbles of the gaseous propellant are formed, rise through the foam and as these gaseous propellant bubbles break the surface of the foam a bubbling auditory sound is produced resulting in a distinct crackling or pinging foam product.

DETAILED DESCRIPTION OF THE INVENTION

The products of this invention can be formed in an aerosol container, for example, by forming an emulsion of the propellant in vehicle with the surfactant at the interface and suspending the zeolite component in the emulsion. The zeolite acts as an adsorbant of the propellant. It is also possible to first form a "concentrate" composition of zeolite, surfactant and vehicle to which can be added from about 15.0 to 60.0% propellant component. When the concentrate is formed first for later addition of the propellant the concentrate composition generally comprises, on a weight basis, from about 24 to about 60.5% zeolite, from about 2 to about 8% surfactant and from about 37.5 to about 74% vehicle. Preferably however such concentrate composition comprises about 40% zeolite, about 4% surfactant and about 56% vehicle.

It will be understood that these are the components required for providing the foamed aerosol compositions characterized by the pronounced and prolonged auditory effect upon discharge from the aerosol container and that the basic auditory foam compositions may have added thereto any active or inactive ingredients which do not adversely affect the foam and auditory characteristics of the composition so as to produce a wide and varied range of products such as, for example, skin and oral care products and cleansers, shampoos and other hair care products, household cleansers, deodorants, shaving creams, after shave lotions, insecticidal sprays, waxes, hair sprays, cosmetics and the like. The examples of such foam products given hereinafter are merely exemplary of such products and in no way restrictive of the type and nature of such desired foam products.

Molecular sieves or zeolites used in the compositions of this invention are crystalline aluminosilicates materials of the following general formula $$M_{2/n}O \cdot SiO_2 \cdot aAl_2O_3 \cdot bH_2O$$

in the salt form where M is a metal cation, ordinarily Na or K but may be other cations substituted by exchange such as calcium or the like, n is the valence of the metal cation, a is the number of moles of alumina and b is the number of moles of hydration.

Molecular sieves or crystalline aluminosilicates are also sometimes referred to as crystalline zeolites and are of both natural and synthetic origin. Natural crystalline aluminosilicates exhibiting molecular sieve activity include for example, analcite, pauling-ite, ptilolite, clinoptilolite, ferrierite, chabazite, genclinite, levynite, erionite and mordenite.

Since not all of the natural crystalline aluminosilicates are available in abundance, considerable attention has been directed to the production of synthetic equivalents. Two basic types of crystalline aluminosilicate molecular sieves most readily available on a commercial scale have been given the artrecognized designations of "Zeolite X" and "Zeolite A". Other molecular sieves which have been synthesized include Zeolites B, F, G, H, K-G, J, L, M, K-M, Q, R, S, T U, Y and Z.

Such molecular sieves or zeolites are described more fully in U.S. Pat. Nos. 3,888,998 and 4,007,134, incorporated herein by reference thereto. More particularly, Zeolite X and Zeolite A and processes for their preparation are described in U.S. Pat. Nos. 2,882,244 and 2,882,243 respectively, both incorporated herein by reference thereto. The zeolite used in the compositions of this invention may be activated zeolites, that is, dehydrated, or hydrous at a level of about 16-34% w/w water.

A wide variety of liquified gases may be employed as the propellant in the crackling foam compositions of this invention. Such liquified gases are liquified hydrocarbon gases and fluorinated hydrocarbons. As examples of such liquified gases there may be mentioned, for example, fluorinated hydrocarbons such as octafluorocyclobutane (FREON C-318), monochloropentafluoroethane (FREON-115), chlorodifluoromethane (FREON-22), dichlorodifluoromethane (FREON-12), 1,2-dichloro-1,1,2,2-tetrafluoroethane (FREON-114), dichloromonofluoromethane (FREON 21), and liquified hydrocarbons such as propane, butane, isobutane, cyclobutane and pentane and the like as well as mixtures of all of such liquified gases. Especially preferred is isobutane which produces a foam product with a high degree of crackling.

The surfactant employed in the foam products of this invention can be any suitable amphoteric, polar non-ionic, non-ionic, zwitterionic, anionic and cationic surfactants or a mixture thereof. This ingredient functions as a lathering and also as a cleansing agent.

Anionic surfactants, that may be employed in the compositions of this invention are water-soluble soap, non-soap synthetic surfactants or mixtures thereof.

Suitable non-soap anionic organic detergents include, for example, water-soluble salts of organic sulfuric reaction products having in their molecular structure an alkyl group containing from about 8 to about 20 carbon atoms and a radical selected from the group consisting of sulfuric acid ester and sulfonic acid radicals. Important examples of this type of non-soap anionic synthetic detergent, include the sodium, potassium ammonium, or alkanolamine alkyl sulfates, especially those derived by sulfation of higher alcohols produced by reduction of tallow or coconut oil glycerides; sodium or potassium alkyl benzene sulfonates, especially those of the types described by Guenther et al. in U.S. Pat. No. 2,220,099, granted Nov. 5, 1940 and by Lewis in U.S. Pat. No. 2,477,383, granted July 26, 1949, in which the alkyl group contains from about 9 to about 15 carbon atoms; sodium alkylglyceryl ether sulfonates, especially those ethers of higher alcohols obtained from tallow and coconut oil; sodium coconut oil fatty acid monoclyceride sulfates and sulfonates; sodium salts of sulfuric acid esters of the reaction product of one mole of a higher fatty alcohol (i.e. tallow or coconut oil alcohols) and about 3 moles of ethylene oxide; and others well known in the art, a number being specifically set forth in Byerly, U.S. Pat. Nos. 2,486,921 and 2,486,922.

Additional non-soap anionic organic synthetic detergents which can be used in this invention include the salts of the condensation products of fatty acids with sarcosine, i.e. acyl sarcosinate, wherein the acyl radical has a chain length range from about 10 to 18 carbon atoms.

Preferably, the non-soap anionic organic detergent will be of the high sudsing type as for example, the alkylglyceryl-ether sulfonates, the sulfated fatty alcohols or the alkyl ether ethylene oxide sulfates wherein the ethylene oxide chain averages 3 units, and acyl sarcosinates, all as more fully set forth above. These and the foregoing detergents can be used in the form of their sodium, potassium, ammonium or lower alkanolamine such as triethanolamine salts.

Conventional soaps may also be used as the anionic detergent component of this invention. Suitable soaps include the sodium, potassium, and lower alkanolamine salts of higher fatty acids of naturally occurring vegetable or animal fats and oils. For example, sodium, potassium and triethanolamine salts of fatty acids occurring in coconut oil, soybean oils, castor oil or tallow, or salts of synthetically produced fatty acids may be used.

A preferred anionic surfactant is the triethanolamine salt of coconut fatty acid, since it is more readily soluble than the salts of higher alkyl chain length fatty acids. Other preferred anionic surfactants include the sodium and potassium salts of coconut fatty acid; sodium lauryl diethoxy sulfate; triethanol amine lauryl sulfate and sodium dodecyl sulfate.

Polar non-ionic detergents can be used in compositions of the invention, either by themselves or in conjunction with an amphoteric detergent. By polar non-ionic detergent is meant a detergent in which the hydrophilic group contains a semi-polar bond directly between two atoms, e.g. $N \rightarrow O$ and $P \rightarrow O$. There is charge separation between the two directly bonded atoms, but the detergent molecule bears no net charge and does not dissociate into ions at neutral pH.

Suitable polar non-ionic detergents include openchain aliphatic amine oxides of the general formula $R_1R_2R_3N \rightarrow O$. The arrow is a conventional representation of a semi-polar bond. These compounds are generally prepared by the direct oxidation of the appropriate tertiary amine. When $R_1$ is a much longer chain than $R_2$ and $R_3$, the amine oxides have surface activity. For the purpose of this invention, $R_1$ is an alkyl, alkenyl or monohydroxyalkyl radical having from about 10 to about 16 carbon atoms. Desirable surface active properties are lost if $R_1$ is substantially less than about 10 carbon atoms and the compounds are insufficiently soluble if $R_1$ is greater than about 16 carbon atoms. $R_2$ and $R_3$ are each selected from the group consisting of methyl, ethyl, propyl, ethanol and propanol radicals. Preferably $R_1$ is a dodecyl radical or a mixture of dodecyl with decyl, tetradecyl and hexadecyl such that at least 50% of the radicals are dodecyl radicals. $R_2$ and $R_3$ are preferably methyl radicals. A preferred amine oxide for the purpose of this invention is a dodecyldimethylamine oxide.

Other operable polar non-ionic detergents are the open chain aliphatic phosphine oxides having the general formula $R_1R_2R_3P \rightarrow O$, wherein R is an alkyl, alkenyl or monohydroxyalkyl radical ranging in chain length from 10 to 18 carbon atoms, and $R_2$ and $R_3$ are each alkyl and monohydroxy-alkyl radicals containing from 1 to 3 carbon atoms. A preferred phosphine oxide is dodecyldimethyl phosphine oxides.

As hereinbefore stated, amphoteric detergents can be used in compositions of the invention, either in conjunction with or in place of the polar non-ionic detergents described above. As used herein, the term "amphoteric" is interchangeable with the term "ampholytic". Amphoteric detergents are well known in the art and many operable detergents of this class are disclosed by A. M. Schwartz, J. W. Perry and J. Birch in "Surface Active Agents and Detergents", Interscience Publishers, New York 1958, Vol. 2. Examples of suitable amphoteric detergents include, for example, alkyl betaiminodipropionates, RN(C₂H₄COOM)₂; alkyl betaamino propionates, RN(H)C₂H₄COOM; and long chain imidazole derivatives having the general formula:

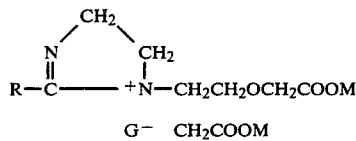

In each of the above formulae R is an acyclic hydrophobic group containing from about 8 to about 18 carbon atoms; G is a hydroxyl, chloride, sulfate or surface active sulfate or sulfonate group and M is a cation to neutralize the charge of the anion. Specific operable amphoteric detergents include the disodium salt of lauroylcycloimidinium-1-ethoxyethionic acid-2-ethionic acid, dodecyl beta alanine, and the inner salt of 2-trimethylamino lauric acid. The substituted betaines and sultaines, such as alkyl ammonio acetates wherein the alkyl radical contains from about 12 to 18 carbon atoms can also be used. The betaine and sultaine types of ampholytic detergents are zwitterionic quaternary ammonium compounds having a general formula:

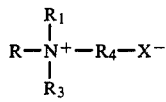

wherein R₁ is an alkyl having from about 10 to about 18 carbon atoms, R₂ and R₃ are each alkyl having from about 1 to about 3 carbon atoms, R₄ is an alkylene or hydroxyalkylene having from 1 to 4 carbon atoms, and X is an anion selected from the group consisting of —SO₃⁻ and —COO⁻.

Compounds which conform to the above general formula are characterized by the presence of both positive and negative charges which are internally neutralized (i.e. zwitterionic). When the anion X is —SO₃⁻, the compounds are referred to as "sultaines". The term "betaines" is employed when the anion X is —COO⁻. The following structural formulae are illustrative of the two types and their inner salt character.

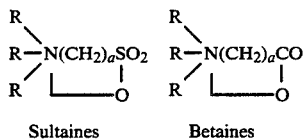

Sultaines    Betaines

When one R in the above formulae is a high weight alkyl having from about 10 to 18 carbon atoms, these compounds are surface active and have good detergency powers. If the high molecular weight alkyl contains less than about 10 carbon atoms, surface activity and detergency are inadequate. If this group contains more than about 18 carbon atoms, the compounds are not sufficiently soluble to be of utility in this invention. Preferably, the high molecular alkyl will contain from 12 to 16 carbon atoms or a mixture of dodecyl with decyl, tetradecyl, and hexadecyl radicals. A convenient source of a suitable mixture of alkyl groups is the middle cut of coconut fatty alcohol which has the approximate chain length composition: 2%-C₁₀, 66%-C₁₂, 23%-C₁₄, and 9%-C₁₆. Particular advantage can be gained by employing betaine or sultaines having an alkyl containing 16 carbon atoms in the compositions of this invention. The alkyl can, of course, contain one or more intermediate linkages such as ether or polyether linkages or non-functional substituents such as hydroxyl or halogen which do not substantially affect the hydrophobic character of the group.

Preferred compounds which fall with the above class include 1-(alkyldimethylammonio)acetate, 1-(alkyldimethylammonio)propane-3-sulfonate and 1-(alkyldimethylammonio)-2-hydroxy-propane-3-sulfonate wherein the alkyl contains from 12 to 16 carbon atoms.

The especially preferred surfactant for use in the crackling foam compositions of this invention are, nonoxyl 6 phosphate as an anionic surfactant, isostearamide amide DEA as non-ionic surfactant, cocaimidopropyl betaine as an amphoteric surfactant and a tris alkylamido tri quaternary as a cationic surfactant.

The vehicle to be employed in the crackling foam compositions of this invention is selected from alkylene glycols, polyalkylene glycols and vegetable oils and mixtures thereof. As examples there may be mentioned, for example, propylene glycol, dipropylene glycol, polypropylene glycol 2000, 4000, polyethylene glycol 200-600, glycerol, 2-methyl-2,4-pentanediol, 1,3-butylene glycol, 1,2,6-hexanetriol, 2-ethyl-1,3-hexanediol, and the like and vegetable oils such as safflower, castor, sesame, olive, soybean, cottonseed and peanut oil and the like. Especially preferred are polyethylene glycol 200 and safflower oil.

The crackling foam compositions of this invention are anhydrous except for the water of hydration present in the zeolites.

As indicated earlier in order to produce any specific type of crackling foam aerosol product according to this invention the crackling foam composition of this invention can have added thereto any active or inactive for such type of product and which do not unduly adversely affect the foam and auditory characteristics of the basic compositions of this invention.

The following are examples of typical product application of the aerosol crackling foam compositions of this invention. It will be appreciated that these examples are merely illustrative and not limiting of the many possible product applications of such crackling foam compositions. In the example the percentage and parts are expressed as percent by weight and parts by weight.

EXAMPLE 1

Skin Cleanser

Seventy parts of a skin cleanser composition comprising:
safflower oil: 1%
nonoxynol 6 phosphate: 3%
cocamide DEA: 1%
polyethylene glycol 200: 55%
sodium zeolite A: 40%
is pressurized in an aerosol container with thirty parts of isobutane propellant to produce a foamable product of the following composition:
safflower oil: 0.7%
nonoxynol 6 phosphate: 2.1%
cocamide DEA: 0.7% polyethylene glycol 200: 38.5%
sodium zeolite A: 28.0%
isobutane: 30.0%

Upon discharge of this product from the aerosol container the composition produces a crackling foam with a pronounced and prolonged auditory effect and can be used as a skin cleanser.

EXAMPLE 2

Hair Shampoo

Seventy parts of a shampoo composition comprising:
sodium lauryl sulfate: 8.5%
lauramide DEA: 2.0%
polyethylene glycol: 49.5%
sodium zeolite A: 40.0%
is pressurized in an aerosol container with 30 parts isobutane propellant to produce a foamable shampoo product of the following composition:
sodium lauryl sulfate: 5.95%
lauramide DEA: 1.40%
polyethylene glycol 200: 34.65%
sodium zeolite A: 28.00%
isobutane: 30.00%

Upon discharge of the product from the aerosol container upon wetted hair the composition produces a crackling foam with a pronounced and prolonged auditory effect and can be used as a shampoo by rubbing on the hair and then rinsing off when desired.

EXAMPLE 3

Household Cleanser

Seventy parts of a household cleanser composition comprising:
nonoxynol 9: 15%
lauramide DEA: 2%
polyethylene glycol 200: 43%
sodium A zeolite: 40%
is pressurized in an aerosol container with 30 parts of isobutane propellant to produce a foamable product of the following composition:
nonoxynol 9: 10.5%
lauramide DEA: 1.4%
polyethylene glycol 200: 30.1%
sodium A zeolite: 28.0%
isobutane: 30%

Upon discharge of the product from the aerosol container the composition produces a crackling foam with a pronounced and prolonged auditory effect and can be used to clean metallic or ceramic surfaces.

EXAMPLE 4

Seventy parts of a composition comprising:
dehydrated sodium zeolite A: 40%
nonoxynol 6 phosphate: 4%
polyethylene glycol 200: 56%
is pressurized in an aerosol container with 30 parts butane propellant to produce a foamable product of the following composition:
dehydrated sodium zeolite A: 28.0%
nonoxynol 6 phosphate: 2.8%
polyethylene glycol 200: 39.2%
butane: 30%

Upon discharge of the product from the aerosol container the composition produces a crackling foam with a pronounced and prolonged auditory effect.

EXAMPLE 5

A similar crackling foam composition is produced when the 30 parts butane propellant of Example 4 is replaced with 30 parts of a propane/isobutane mixture propellant.

EXAMPLE 6

A similar crackling foam composition is produced when the 30 parts butane propellant of Example 4 is replaced with 30 parts of a 20:80 mixture of tetrafluorodichloroethane and dichlorodifluoromethane propellant.

EXAMPLES 7-9

When the dehydrated sodium zeolite A of Examples 4 through 6 are replaced with an equivalent amount of hydrated sodium zeolite A (20% water) similar crackling foam compositions producing pronounced and prolonged auditory effects are obtained.

EXAMPLE 10

When the polyethylene glycol 200 vehicle of the composition of Example 4 is replaced with an equivalent amount of safflower oil a similar crackling foam position producing a pronounced and prolonged auditory effect is obtained.

EXAMPLE 11

When the nonoxynol 6 phosphate anionic surfactant of the composition of Example 4 is replaced with an equivalent amount of isostearamide DEA nonionic surfactant a similar crackling foam composition producing a pronounced and prolonged effect is obtained.

EXAMPLE 12

When the nonoxynol 6 phosphate anionic surfactant of the composition of Example 4 is replaced with an equivalent amount of tris alkylamido tri quaternary cationic surfactant a similar crackling foam composition producing a pronounced and prolonged auditory effect is obtained.

EXAMPLE 13

When the nonoxynol 6 phosphate anionic surfactant of Example 4 is replaced with an equivalent amount of cocamidopropyl betaine amphoteric surfactant a similar crackling foam composition producing a pronounced and prolonged auditory effect is obtained.

We claim:

1. An aerosol foam composition producing pronounced and prolonged auditory effects upon discharge from an aerosol container comprising, as percent by weight,
molecular sieve about 16 to about 34%,
surfactant about 1.6 to about 3.4%,
vehicle about 22.4% to about 47.6%,
liquified gas propellant, about 15 to about 60%,
and wherein the vehicle is selected from the group consisting of alkylene glycols, polyalkylene glycols, vegetable oils and mixtures thereof and the liquified gas propellant is selected from the group consisting of liquified hydrocarbon and fluorinated hydrocarbon gases.

2. An aerosol foam composition of claim 1 wherein the vehicle comprises polyethylene glycol 200.

3. An aerosol foam composition of claim 2 wherein the liquified gas propellant is isobutane.

4. An aerosol foam composition of claim 3 wherein the molecular sieve is sodium zeolite A.

5. An aerosol foam composition of claim 4 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

6. An aerosol foam composition of claim 3 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

7. An aerosol foam composition of claim 2 wherein the molecular sieve is sodium zeolite A.

8. An aerosol foam composition of claim 7 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

9. An aerosol foam composition of claim 8 wherein the liquified gas propellant is selected from the group consisting of butane, isobutane, propane, tetrafluorodichloroethane and dichloromonofluoromethane and mixtures thereof.

10. An aerosol foam composition of claim 2 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

11. An aerosol foam composition of claim 1 wherein the liquified gas propellant is isobutane.

12. An aerosol foam composition of claim 11 wherein in the molecular sieve is sodium zeolite A.

13. An aerosol foam composition of claim 12 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

14. An aerosol foam composition of claim 11 wherein the sufactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

15. An aerosol foam composition of claim 1 wherein the molecular sieve is sodium zeolite A.

16. An aerosol foam composition of claim 15 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

17. An aerosol foam composition of claim 1 wherein the surfactant comprises a compound selected from the group consisting of nonoxynol-6-phosphate, cocamide DEA, lauramide DEA, sodium lauryl sulfate, isostearamide DEA, cocamidopropyl betaine and tris alkylamido tri quaternary.

18. An aerosol foam composition of claim 1 which is a skin cleanser product comprising:
safflower oil about 0.7%
nonoxynol 6 phosphate about 2.1%
cocamide DEA about 0.7%
polyethylene glycol 200 about 38.5%
sodium zeolite A about 28.0%
isobutane about 30.0%.

19. An aerosol foam composition of claim 1 which is a shampoo product comprising:
sodium lauryl sulfate about 5.95%
lauramide DEA about 1.40%
polyethylene glycol 200 about 34.65%
sodium zeolite A about 28.00%
isobutane about 30.00%

20. An aerosol foam composition of claim 1 which is a household cleanser product comprising:
nonoxynol 9 about 10.5%
lauramide DEA about 1.4%
polyethylene glycol 200 about 30.1%
sodium A zeolite about 28.0%
isobutane about 30.0%

* * * * *